United States Patent
Lechner

(10) Patent No.: US 8,343,032 B2
(45) Date of Patent: Jan. 1, 2013

(54) CONTROLLABLE GASTRIC BAND

(76) Inventor: Wolfgang Lechner, Judenau/Pixendorf (AT)

( * ) Notice: Subject to any disclaimer, the term of this patent is extended or adjusted under 35 U.S.C. 154(b) by 440 days.

(21) Appl. No.: 12/353,600

(22) Filed: Jan. 14, 2009

(65) Prior Publication Data

US 2009/0118572 A1 May 7, 2009

Related U.S. Application Data

(62) Division of application No. 10/565,793, filed as application No. PCT/AT2004/000265 on Jul. 23, 2004, now Pat. No. 7,530,943.

(30) Foreign Application Priority Data

Jul. 25, 2003 (AT) ................................ A 1180/2003
Feb. 24, 2004 (AT) ................................. A 284/2004

(51) Int. Cl.
  *A61F 2/00* (2006.01)
(52) U.S. Cl. ........................................................ 600/37
(58) Field of Classification Search .................... 600/29, 600/37; 623/23.64–23.67; 606/151; 128/897, 128/899
See application file for complete search history.

(56) References Cited

U.S. PATENT DOCUMENTS

| | | | |
|---|---|---|---|
| 4,399,809 A | 8/1983 | Baro et al. | |
| 4,592,339 A | 6/1986 | Kuzmak et al. | |
| 5,690,691 A | 11/1997 | Chen et al. | |
| 5,983,669 A | 11/1999 | Karmeli | |
| 6,432,040 B1 | 8/2002 | Meah | |
| 6,460,543 B1 | 10/2002 | Forsell | |
| 6,475,136 B1 | 11/2002 | Forsell | |
| 7,037,343 B2 | 5/2006 | Imran | |
| 2001/0011543 A1 | 8/2001 | Forsell | |

FOREIGN PATENT DOCUMENTS

| | | |
|---|---|---|
| EP | 0 028 962 | 4/1984 |
| EP | 0876808 | 11/1998 |
| JP | 56-76945 | 6/1981 |
| WO | 01/24742 | 4/2001 |
| WO | 03/020183 | 3/2003 |
| WO | 2004/014245 | 2/2004 |

OTHER PUBLICATIONS

English abstract of EP 0876808 dated Nov. 11, 1998.
English abstract of WO 01/24742 dated Apr. 12, 2001.

*Primary Examiner* — Christine Matthews
(74) *Attorney, Agent, or Firm* — Ladas & Parry LLP

(57) ABSTRACT

The invention relates to an adjustable stomach band with a rigid back and a chamber, arranged on the stoma side of the back, for control of stoma constriction by means of introduction or removal of fluid from the chamber. According to the invention, such a stomach band with a preferably automatic setting of the stoma constriction, depending on the food intake, is possible, whereby a second chamber is provided to the stoma side of the back, directly connected to, or cooperating with the first chamber, such that the control of the stoma constriction is achieved by means of displacing the fluid between the chambers or between a reservoir and the stoma-constricting chamber. An auto-regulation can be achieved, whereby a second chamber is embodied as sensor for recording a pressure rise in the stomach and the control of the stoma constriction is achieved depending on the recorded pressure by means of displacement of the fluid from the chamber, or from the reservoir into the stoma-constricting chamber.

12 Claims, 3 Drawing Sheets

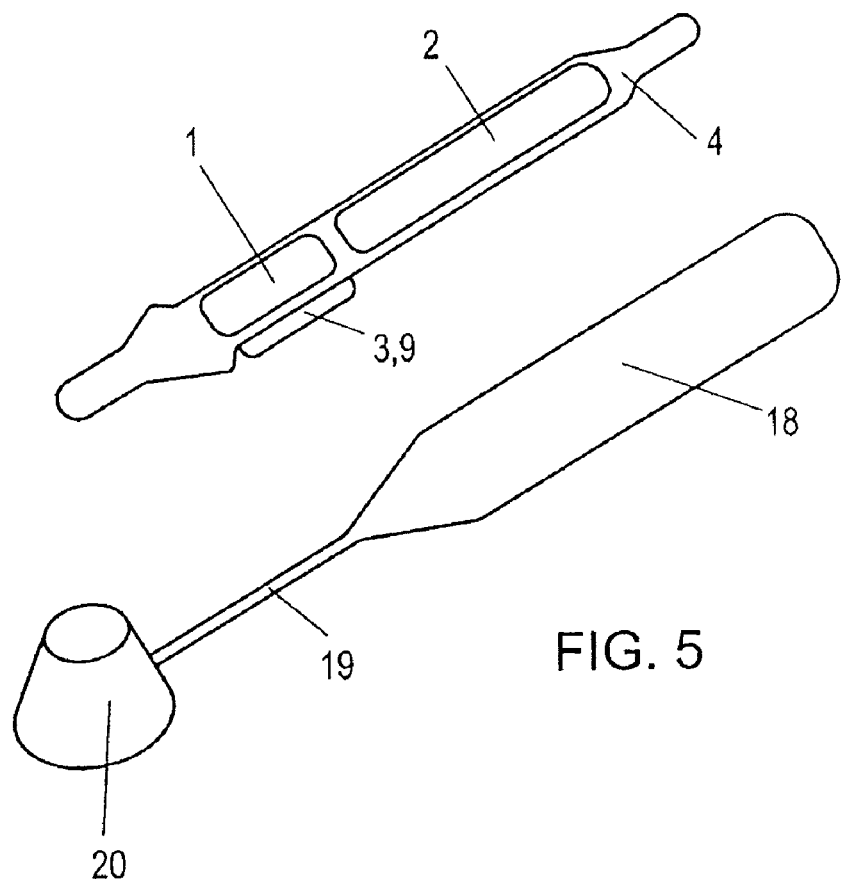
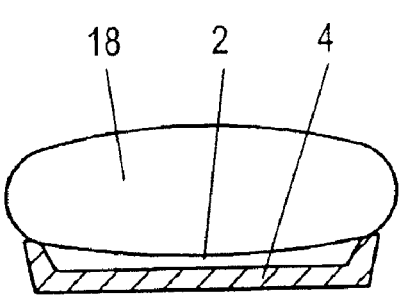
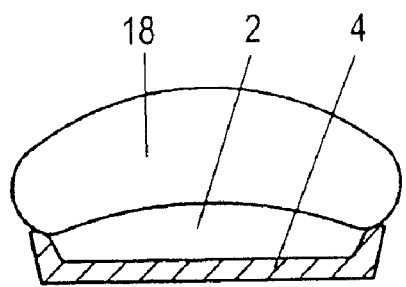
FIG. 5
FIG. 6a  FIG. 6b

CONTROLLABLE GASTRIC BAND

This application is a divisional of application Ser. No. 10/565,793 filed on Jan. 25, 2006 now U.S. Pat. No. 7,530,943, which is a 371 of International Application AT2004/000265 filed on Jul. 23, 2004, which designated the U.S., claims the benefit thereof, and incorporates the same by reference.

The invention relates to a controllable gastric band including a nonextensible back and a chamber arranged on the stoma side of the back, for controlling the restriction of the stoma by supplying and discharging liquid to and from said chamber.

The invention is directed to a further development of the controllable gastric band offered by several manufacturers in basically identical structural shapes (e.g., Swedish band by Obtech (Johnson & Johnson), Lapband by Bioenterics, ... ). This is a band used to restrict food intake, which is wrapped around the uppermost portion of the stomach or esophagus and closed.

WO 01/24742 A1 describes a gastric band which is positioned around the stomach and secured like a belt. The adjustment of the stoma restriction is feasible in a purely mechanical manner by contracting the band.

U.S. Pat. No. 4,592,339 A describes a gastric band in which a chamber is arranged on the band side facing the stomach, which can be filled with liquid. A control of the stoma width is thus feasible. The filling with liquid and emptying of the system may be realized through a subcutaneously sewn-in port which is connected with the chamber of the gastric band via a flexible hose.

Finally, WO 03/020183 A1 discloses a gastric band which is surrounded by a viscoelastic material to spare the stomach.

The majority of presently used gastric bands yield very good long-term results in terms of weight reduction and patient satisfaction. Yet, there are some problems, which will become particularly predominant with high band fillings. Many patients have, thus, reported about unpleasant phenomena like sialemesis and regurgitation, above all, in the recumbent position. Food particles may remain in the esophagus above the stoma for a long time, start fermenting there and, hence, provoke, in addition to bad breath, an irritation of the mucous membrane involving pain. As in the event of achalasia, the permanently existing narrow position of the stoma will lead to an increasing expansion of the esophagus over months, finally causing the esophagial sensitivity to disappear and the band effect to be lost, which will subsequently lead to an increase in weight despite the highly filled gastric band provided.

The problem faced with presently employed gastric bands consists in that the chosen filling level and, hence, the stoma width will constantly remain the same although only a restricted food intake is sought.

Departing from the prior art with the presently used gastric band, the invention aims to provide a gastric band that enables the preferably automatic adjustment of the stoma width. What is aimed at is a gastric band that is set to be narrow only during food intake, yet, for the remaining time, is wide enough not to produce any negative secondary effects. The band is to contract during eating and expand again after having stopped the ingestion of food.

The object according to the invention, on the one hand, is achieved in that a second chamber is provided on the stoma side of the back, which second chamber communicates with the first chamber in a manner to ensure the control of the stoma restriction by a displacement of the liquid between the one chamber and the other chamber. A regulation of the gastric band and, hence, of the stoma restriction is, thus, feasible by a displacement of the liquid between two chambers without adding or diverting liquid from or to the outside. The unequal distribution of the liquid between the two chambers will cause a narrower stoma at the level of the higher filled chamber. Thereby, a gastric band including a liquid circulation is provided.

The object according to the invention is also achieved in that a second chamber is provided on the stoma side of the back, which second chamber is designed as a sensor for the detection of a pressure increase in the stomach or esophagus, and that the other chamber via the sensory chamber is connected with a reservoir in a manner to ensure the control of the stoma restriction by a displacement of the liquid between the reservoir and the stoma-restricting chamber as a function of the pressure detected by the sensory chamber. This embodiment provides a double-circulation system with the sensory chamber constituting a liquid space and the stoma-restricting chamber, together with the reservoir, constituting the second liquid space. Unlike with a single-chamber circulation system, in which a liquid displacement from the one chamber into the other chamber takes place, a displacement of the liquid from the reservoir into the stoma-restricting chamber, and vice versa, is, thus, provided as a function of the pressure detected by the sensory chamber. The two chambers are, therefore, in an active connection with each other.

In a preferred manner, the chambers are arranged one beside the other, with the stoma-restricting chamber being located aborally.

The second chamber may also be subdivided into two communicating chambers delimiting the stoma-restricting chamber on either side. The stability of the gastric band is thereby increased.

It is likewise feasible that the chambers are arranged one above the other in respect to the stomach or esophagus, with the sensory chamber being arranged on the gastric wall.

A layer may be provided between the chambers.

A device for pumping liquid is preferably provided to displace the liquid from one chamber, or the reservoir, into the stoma-restricting chamber, and vice versa.

The pumping device is comprised of an electrically or mechanically driven pump such as, for instance, a lift-and-force pump. If a mechanically driven pump such as, for instance, a lift-and-force pump is employed, the energy taken up by the sensory chamber is used to inflate the stoma-restricting chamber.

In order to achieve an auto-regulation of the stoma restriction by the aid of the gastric band, a device for detecting the eating activity is advantageously provided.

The detection of the eating activity may be realized by a detection of the deglutition activity, a detection of the pressure prevailing at the gastric wall or wall of the esophagus, or by a detection of the peristaltic wave. To detect the pressure prevailing at the gastric wall or wall of the esophagus, a pressure sensor connected to an electronic circuit may be provided in the sensory chamber.

According to a further characteristic feature of the invention, it is provided that the detection device is connected with the pumping device in a manner that, after having detected the eating activity, liquid is pumped from the sensory chamber, or reservoir, into the stoma-restricting chamber and the liquid is again returned from the stoma-restricting chamber into the second chamber, or reservoir, at a given time after the detection of a stop of the eating activity. This enables an automatic stoma restriction to occur as a function of the food intake.

According to a variant embodiment of a gastric band having but one liquid circulation in a purely mechanical fashion, the chambers are connected with each other via an auxiliary chamber functioning as an air chamber, wherein a valve is arranged between the second chamber and the auxiliary chamber, which valve allows the transport of liquid only from the second chamber to the auxiliary chamber, and wherein a further valve is arranged between the auxiliary chamber and the stoma-restricting chamber, which further valve allows the transport of liquid only from the auxiliary chamber to the stoma-restricting chamber.

In the event of a gastric band including two liquid circulations, an auxiliary chamber functioning as an air chamber may likewise be arranged in the connection between the reservoir and the stoma-restricting chamber. It is thereby feasible to temporarily store, for a short time, the energy produced by a pressure increase in the stomach or esophagus and use the same only subsequently to inflate the stoma-restricting chamber. It is thereby achieved that the stoma-restricting chamber is only activated after the peristaltic wave has subsided.

In order to enable a liquid exchange between the stoma-restricting chamber and the second chamber or reservoir, respectively, a device for carrying out a liquid exchange from the stoma-restricting chamber to the second chamber or reservoir, respectively, is provided.

Said device for carrying out a liquid exchange from the stoma-restricting chamber to the second chamber or reservoir, respectively, may be comprised of a common partition wall arranged between the chambers or chamber and reservoir, respectively, and containing micropores. Through these micropores contained in the partition wall between the adjacently arranged chambers of the gastric band or chamber and reservoir, respectively, a slow continuous liquid exchange takes place.

The device for carrying out a liquid exchange may, however, also be comprised of a back flow channel arranged between the chambers or the stoma-restricting chamber and reservoir, respectively.

Within the same, a throttle valve or the like may be arranged to throttle the liquid flow, permitting it in only one direction.

According to a further characteristic feature of the invention, it is provided that the sensory chamber is connected to a stomach pacemaker or a device emitting electric pulses so as to obtain a stimulation of the gastric wall by electric pulses as a function of the pressure prevailing in the stomach or esophagus and detected by the sensory chamber. A stimulation of the stomach or esophagus can thereby be carried out during food intake.

In addition, a further liquid-filled chamber may be provided for the adaptation of the gastric band, which chamber has neither a sensing nor a stoma-restricting function in the context of the controllable gastric band, but serves to adapt the gastric band to the respective circumstances. Said further chamber is arranged above the sensory and stoma-restricting chambers of the gastric band and jointly wrapped around the uppermost stomach portion or esophagus and secured.

In an advantageous manner, said further chamber is connected with a port to be subcutaneously arranged in a manner to allow liquid to be filled into, or removed from, said chamber by supplying or discharging liquid through said port and, hence, enable an adaptation of the gastric band. Naturally, also several chambers may be provided to adaptat the gastric band.

The invention will be explained in more detail by way of the attached Figures.

Therein:

FIG. 5 is a perspective view of a further embodiment of a controllable gastric band; and FIGS. 6a and 6b are sectional views through the gastric band of FIG. 5 with different filling levels of the stoma-restricting chamber.

Figure 1:
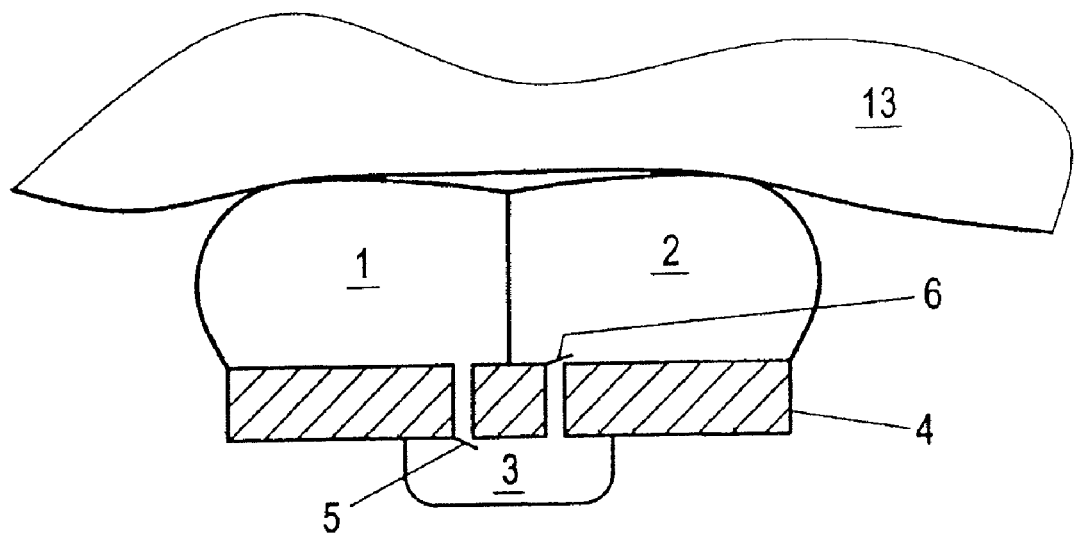
FIG. 1 is a schematic cross section through an embodiment of a gastric band including a liquid circulation in the state of an equal distribution of the liquid filling in the two chambers.
Figure 2:
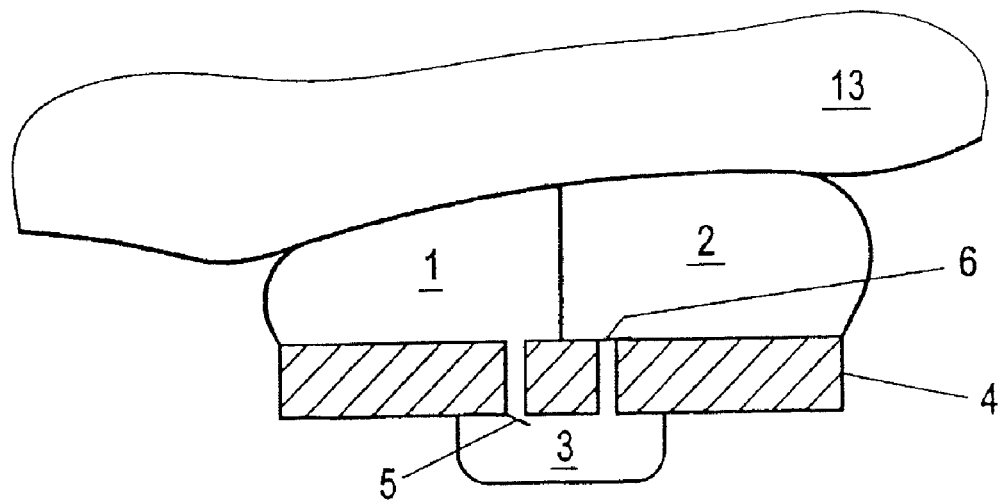
FIG. 2 is a schematic cross section through the gastric band according to FIG. 1 after the displacement of liquid into the stoma-restricting chamber.

The gastric band illustrated in FIGS. 1 and 2 comprises a nonextensible back 4 like the bands presently in use. On the side of the back 4 facing the gastric wall 13, two chambers 1, 2 are arranged to be interconnected in a manner to enable a displacement of liquid between chambers 1 and 2. The chambers 1, 2 facing the gastric wall 13 extend circularly around the stomach or esophagus like in conventional gastric bands including just one chamber. In the exemplary embodiment illustrated, an auxiliary chamber 3 functioning as an air chamber is provided on the outer side of the back 4 facing away from the gastric wall 13. The auxiliary chamber 3 is connected with the two chambers 1, 2. A valve 5 arranged between the chamber 1 and the auxiliary chamber 3 permits the outflow of liquid from the chamber 1 into the auxiliary chamber 3. A further valve 6 arranged between the stomach-restricting chamber 2 and the auxiliary chamber 3 permits the outflow of liquid from the auxiliary chamber 3 into the stomach-restricting chamber 2. The passage of solid food through the stoma, thus, causes an increase in the pressure prevailing in the two chambers 1, 2 bordering on the gastric wall 13, from a resting pressure p1 to a pressure p2. Liquid is, thus, pressed from the chamber 1 into the auxiliary chamber 3. The valve 5 prevents a backflow from the auxiliary chamber 3 into the chamber 1. On account of its function as an air chamber, the auxiliary chamber 3 stores the elevated pressure p2. After the passage of a bite through the stoma, the liquid pressure in the two gastric-wall-near chambers 1 and 2 again drops to the resting pressure p1. The auxiliary chamber 3, which is under the elevated pressure p2, subsequently evacuates the liquid into the stoma-restricting chamber 2. In this case, liquid is, thus, displaced from the chamber 1 into the stoma-restricting chamber 2 via the purely mechanical pumping mechanism caused by the passage of solid food through the stoma. The stoma opening at the level of the chamber 2 is thereby narrowed, as is schematically illustrated in FIG. 2. The displacement of the liquid occurs continuously during eating. Following eating the band is widened again after a predetermined time, by a backflow from the stoma-restricting chamber 2 into the chamber 1 being triggered. The optimum time for this liquid exchange must be determined in clinical studies. The exemplary embodiment according to FIGS. 1 and 2 comprises a gastric band including a liquid circulation formed through chambers 1, 2 and the auxiliary chamber 3. In the example illustrated, the liquid exchange takes place via micropores provided in the partition wall between the adjacently arranged chambers 1 and 2. In this manner, a slow continuous liquid exchange occurs. The pumping procedures may be controlled either electronically or mechanically.

The aim of the autoregulatory change of the stoma width is, thus, achieved by a displacement of the liquid from one chamber into the other chamber. Unlike the initial state of the liquid amount equally distributed in the two chambers, an unequal distribution implies a stoma restriction in the region of one chamber and a stoma expansion at the level of the other chamber. In terms of effect on the bearer of the gastric band, this means a stoma restriction and, hence, a complication of the eating procedure.

Figure 3:
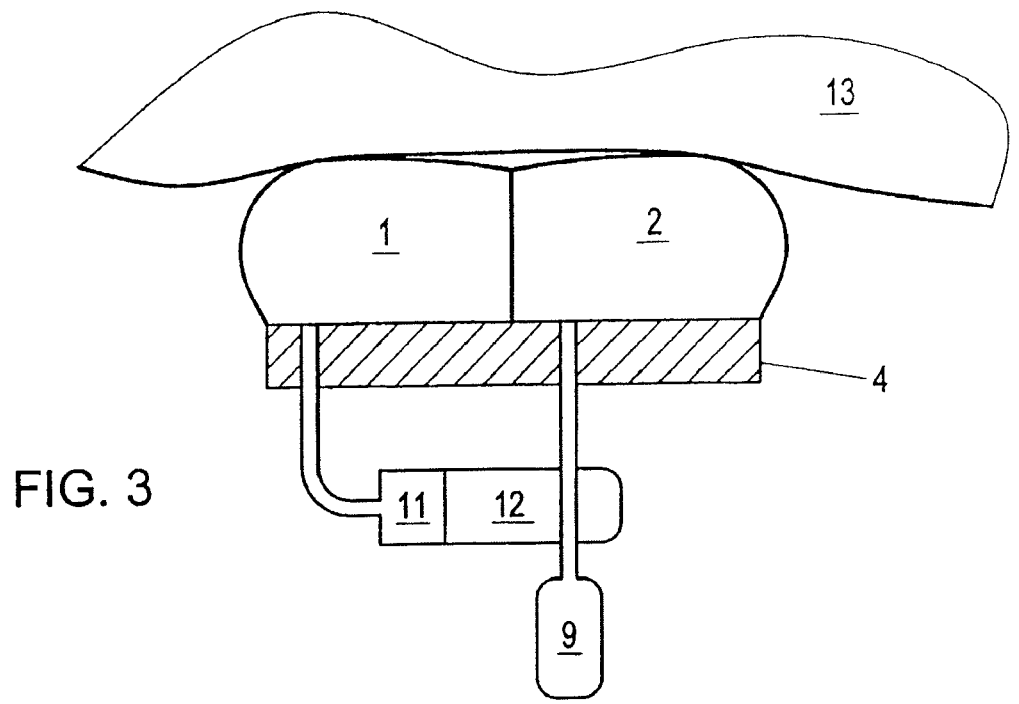
FIG. 3 is a schematic cross section through a further, embodiment of a controllable gastric band including two liquid circulations and an electrically driven pump.
Figure 4:
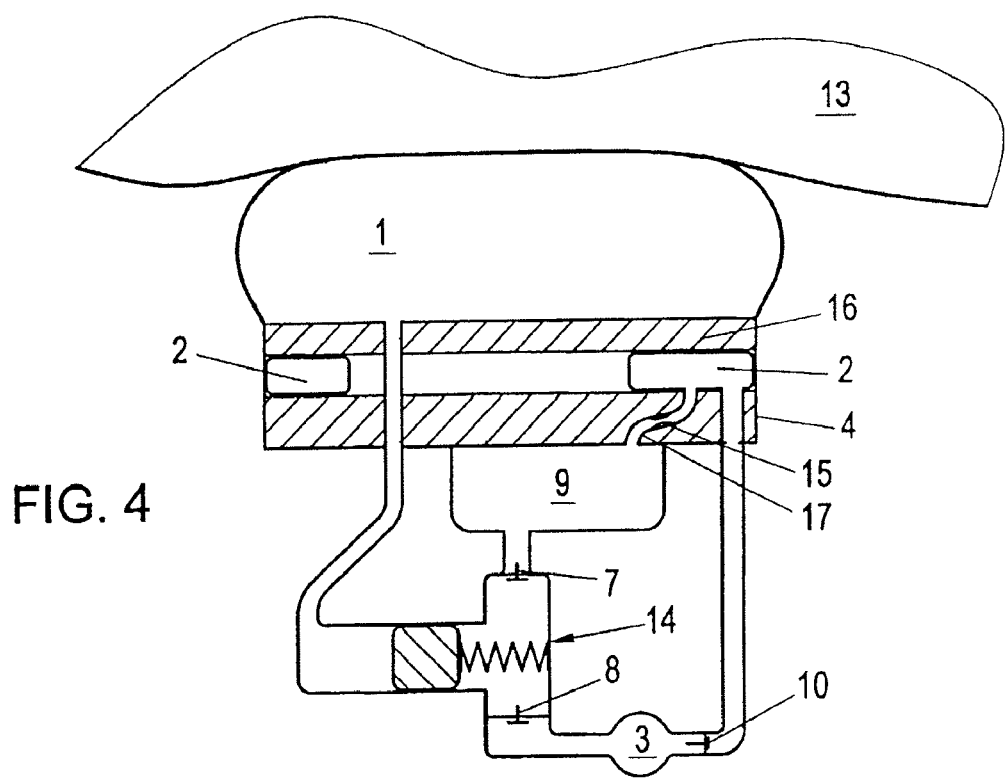
FIG. 4 is a schematic cross section through a further mechanical embodiment of a controllable gastric band including two liquid circulations.

The embodiments of gastric bands illustrated in FIGS. 3 and 4 are variants for which two liquid circulations are provided. The gastric band has a nonextensible back 4 like the bands presently in use. On the side of the back 4 facing the gastric wall 13, two chambers 1, 2 are located, which are in active connection. The chamber 1, which is arranged cranially relative the stomach, functions as a sensor, detecting the movements of the stomach and esophagus caused during the ingestion of food. The chamber 2 located beside the sensory chamber 1 serves to restrict the stoma and communicates with a reservoir 9. From this reservoir 9, liquid can be pumped into the chamber 2 and, from there, back into the reservoir 9. An electronic circuit 11, for instance, serves to establish the active connection between chambers 1 and 2 by detecting the pressure taken up by the sensory chamber 1, and accordingly triggering an electric pump 12. The electric pump 12 conveys liquid from the reservoir 9 into the chamber 2, thus causing a restriction of the stoma. The restriction of the stoma is, thus, effected after the passage of food has been detected by the chamber 1. During the passage of swallowed food, the pressure within the chamber 1 rises such that a controllable gastric band of conventional design can be used as a sensor for the deglutition activity. The displacement of liquid from the reservoir 9 into the chamber 2 causes a restriction of the stoma, which will widen again at a return displacement of the liquid into the reservoir 9.

FIG. 4 depicts a variant of the controllable gastric band according to the invention, in which the connection between the chamber 1 and the chamber 2 connected with the reservoir 9 is realized via a lift-and-force pump 14. In this instance, the pressure rising in the sensory chamber 1 during the ingestion of food is used to inflate the chamber 2. The liquid in the sensory chamber 1, thus, actuates the lift-and-force pump 14 and, through appropriately arranged valves 7, 8, causes a liquid flow from the reservoir 9 into the chamber 2 and, hence, the inflation of the chamber 2, followed by a restriction of the stoma. Due to the arrangement of an auxiliary chamber 3 functioning as an air chamber, between the valve 8 and a further valve 10, a delayed liquid flow will occur, and hence a delayed restriction of the stoma will be obtained. The backflow of the liquid from the chamber 2 into the reservoir 9 may occur through a backflow channel 17 in which a throttle valve 15 may, for instance, be arranged, which causes the stoma restriction to be slowly released. The pumping mechanism is, thus, deactivated after having finished eating, causing a slow backflow of liquid from the chamber 2 into the reservoir 9. The liquid backflow takes place without consuming any energy because of a pressure gradient prevailing between the stoma-restricting chamber 2 and the reservoir 9. A pressure gradient necessarily exists between the chamber 2 and the reservoir 9, since the reservoir 9 is located outside the back 4 and, therefore, does not participate in the rise of the resting pressure occurring simultaneously with the filling of the stoma-restricting chamber 2.

The variant embodiment according to FIG. 4 further differs from that of FIG. 3 in that the two chambers 1, 2 are arranged one above the other relative to the gastric wall 13. In this case, the chambers 1, 2 are radially superimposed with the sensory chamber 1 being located on the gastric wall 13 or wall of the esophagus and the chamber 2 being arranged above the chamber 1, optionally upon interposition of a layer 16. From the arrangement of chambers 1, 2 one above the other, a pressure situation differing from that with adjacently arranged chambers 1, 2 results. In the event of superimposed chambers 1, 2, no liquid backflow from the stoma-restricting chamber 2 into the sensory chamber 1 would occur with a single-circulation system according to FIGS. 1 and 2 because of the same pressure prevailing in the two chambers 1, 2, since both of said chambers 1, 2 are arranged one above the other between the gastric wall 13 and the back 4. A restriction by a liquid displacement from the sensory chamber 1 into the stoma-restricting chamber 2 will only occur if the stoma-restricting chamber 2 is narrower than the sensory chamber 1. Thus, the pressure gradient problem has, at the same time, been overcome. For the force exerted by the two chambers 1, 2 on the common boundary surface A, F=p·A applies. Due to the larger surface by which the sensory chamber 1 joins the common boundary surface, the force exerted by the sensory chamber 1 is larger than that of the stoma-restricting chamber 2 having a smaller contact surface. The stoma-restricting chamber 2 consequently tends to empty into the sensory chamber 1. After having finished eating, the liquid flows back into the sensory chamber 1 and the stoma width increases again.

No electric energy is needed for the variant including a lift-and-force pump 14 according to FIG. 4. Chambers 1, 2 comprise, for instance, the whole periphery.

As opposed to the single-circulation system according to FIGS. 1 and 2, the double-circulation system according to FIGS. 3 and 4 does not involve any problems in respect to the functioning of the restriction with any arrangement of the chambers 1, 2. Liquid will always be displaced from a reservoir 9 into the stoma-restricting chamber 2, thus necessarily reducing the stoma width. By contrast, in a single-circulation system, the displacement of liquid from the sensory chamber 1 into the stoma-restricting chamber 2 will only cause a stoma restriction, if the chambers 1, 2 are arranged one beside the other. If the two chambers 1, 2 were arranged radially above each other, the displacement of liquid from the one chamber 1 into the stoma-restricting chamber 2 would not lead to any change in the width of the stoma. This will only be reached if the chamber into which the liquid is pumped is designed to be narrower than the chamber from which the liquid is removed. If the stoma-restricting chamber is narrower, it will be higher with the same amount of liquid, and the stoma width will, hence, be smaller. The displacement of liquid from the wider chamber into the narrower chamber will, thus, cause a stoma restriction.

FIG. 5 in a perspective view illustrates a further embodiment of a gastric band, wherein the sensory chamber 1 and the stoma-restricting chamber 2 are arranged on the nonextensible back 4 one beside the other along the periphery of the gastric band. The auxiliary chamber 3, via which the liquid is pumped from chamber 1 to the stoma-restricting chamber 2 or a reservoir 9 connected to the stoma-restricting chamber 2, respectively, is provided outside the back 4. The gastric band is wound around the uppermost portion of the stomach or esophagus and closed. In the exemplary embodiment illustrated, the two chambers 1, 2 each occupy only a portion of the circumference. In addition, a further chamber 18 may be provided, which has neither a sensory nor a stoma-restricting function in the context of the controllable gastric band, but serves to adapt the gastric band to the respective circumstances. To this end, the elongate chamber 18 is arranged above the chambers 1, 2 of the gastric band and, together with the same, is wound around the uppermost portion of the stomach or esophagus and secured. The chamber 18 is connected with a subcutaneously arranged port 20 via a suitable duct 19 in a manner known per se. The adaptation of the gastric band is, thus, feasible by supplying or discharging liquid into or from the chamber 18 via port 20.

FIGS. 6a and 6b illustrate sections through such a gastric band according to FIG. 5 in the region of the stoma-restricting chamber 2. In FIG. 6a, the stoma-restricting chamber 2 is not much filled such that the chamber 18 is pressed against the gastric wall 13 (not illustrated) to a lesser degree than in the situation according to FIG. 6b, in which the stoma-restricting chamber 2 is appropriately filled with liquid and the chamber 18 is, hence, pressed against the gastric wall 13 or wall of the esophagus, whereby a restriction of the stoma is caused. This additional chamber 18 which does not take part in the autoregulatory system, thus, allows for the optimum adaptation of the gastric band from outside via port 20.

The sensory function of the gastric band renders feasible a new approach to the concept of a stomach pacemaker. By combining a gastric band operating as a sensor with a pacemaker, the stimulation of the gastric wall by electric pulses can be limited to the periods of food intake. By the suitable placement of the pacemaker probes in the region of the lower esophagus sphincter, it would also be possible to cause an activation of this constrictor muscle and, hence, a restriction of the food passage. The restriction will then be caused by a physiologically inherent structure rather than the active chamber.

The invention claimed is:

1. In a controllable gastric band including a nonextensible back and a first chamber arranged to be on a stomach or esophagus side of the back for controlling restriction of the stomach or esophagus by supplying and discharging liquid to and from the first chamber, the improvements in that
a second chamber is provided on the stomach or esophagus side of the back, the second chamber being a sensor for detection of a pressure increase in the stomach or esophagus, and
the first chamber is connected via the second chamber with a reservoir chamber in a manner to control the restriction by displacement of the liquid between the reservoir chamber and the first chamber as a function of the detected pressure,
wherein a device for carrying out a liquid exchange from the first chamber to the second chamber or reservoir chamber, respectively, is provided between the first chamber and the second chamber or reservoir chamber, respectively and is comprised of a common partition wall containing micropores and arranged between the chambers or between the first chamber and the reservoir chamber, respectively.

2. The gastric band according to claim 1, wherein an auxiliary chamber functioning as an air chamber is arranged between the reservoir chamber and the first chamber.

3. The gastric band according to claim 1, wherein the first chamber is connected to a stomach pacemaker or a device emitting electric pulses so as to obtain, via appropriately placed probes, a stimulation of the gastric wall by electric pulses as a function of the pressure prevailing in the stomach or esophagus and detected by the first chamber.

4. In a controllable gastric band including a nonextensible back and a first chamber arranged to be on a stomach or esophagus side of the back for controlling restriction of the stomach or esophagus by supplying and discharging liquid to and from the first chamber, the improvements in that
a second chamber is provided on the stomach or esophagus side of the back, the second chamber being a sensor for detection of a pressure increase in the stomach or esophagus, and
the first chamber is connected via the second chamber with a reservoir chamber in a manner to control the restriction by displacement of the liquid between the reservoir chamber and the first chamber as a function of the detected pressure,
wherein a device for carrying out a liquid exchange from the first chamber to the second chamber or reservoir chamber, respectively, is provided between the first chamber and the second chamber or reservoir chamber, respectively and is comprised of a backflow channel arranged between the chambers of the first chamber and the reservoir chamber respectively.

5. The gastric band according to claim 4, wherein the first chamber and the second chamber are arranged one above the other so that they may be disposed in respect to the stomach or esophagus such that the second chamber is on the gastric wall.

6. The gastric band according to claim 5, wherein a layer is provided between the chambers.

7. The gastric band according to claim 4, wherein a pumping device for pumping the liquid from the second chamber or the reservoir chamber into the first chamber and vice versa is provided.

8. The gastric band according to claim 7, wherein the pumping device is at least one of a mechanically driven pump or a lift-and-force pump.

9. The gastric band according to claim 7, wherein a detection device is connected with the pumping device in a manner that, after detecting an eating activity, the liquid is pumped from the second chamber or reservoir chamber into the first chamber and the liquid is again returned from the first chamber into the second chamber or reservoir chamber at a given time after the detecting of the eating activity has stopped.

10. The gastric band according to claim 4, wherein an auxiliary chamber functioning as an air chamber is arranged between the reservoir chamber and the first chamber.

11. The gastric band according to claim 4, wherein a throttle valve is arranged within the backflow channel.

12. The gastric band according to claim 4, wherein the first chamber is connected to a stomach pacemaker or a device emitting electric pulses so as to obtain, via appropriately placed probes, a stimulation of the gastric wall by electric pulses as a function of the pressure prevailing in the stomach or esophagus and detected by the first chamber.

* * * * *